United States Patent
Yamamoto et al.

(10) Patent No.: US 8,123,729 B2
(45) Date of Patent: Feb. 28, 2012

(54) TREATMENT OF OCULAR DISEASE

(75) Inventors: Ronald K. Yamamoto, San Francisco, CA (US); Stanley R. Conston, San Carlos, CA (US); Michael F. Nash, Danville, CA (US); Paul S. Koch, Warwick, RI (US)

(73) Assignee: iScience Interventional Corporation, Menlo Park, CA (US)

( * ) Notice: Subject to any disclaimer, the term of this patent is extended or adjusted under 35 U.S.C. 154(b) by 17 days.

(21) Appl. No.: 12/587,375

(22) Filed: Oct. 5, 2009

(65) Prior Publication Data
US 2010/0179652 A1     Jul. 15, 2010

Related U.S. Application Data

(62) Division of application No. 09/735,408, filed on Dec. 11, 2000, now abandoned.

(60) Provisional application No. 60/172,693, filed on Dec. 10, 1999.

(51) Int. Cl.
*A61M 35/00*     (2006.01)

(52) U.S. Cl. .................. 604/294; 606/4; 606/6
(58) Field of Classification Search .............. 604/294; 606/4, 6, 108, 130; 600/461
See application file for complete search history.

(56) References Cited

U.S. PATENT DOCUMENTS

| 5,906,580 A * | 5/1999 | Kline-Schoder et al. ...... 600/459 |
| 6,203,499 B1 * | 3/2001 | Imling et al. .................. 600/461 |

\* cited by examiner

*Primary Examiner* — Laura Bouchelle
(74) *Attorney, Agent, or Firm* — GSS Law Group; James J. Leary; Carol D. Titus

(57) ABSTRACT

The invention relates to a novel apparatus for the treatment of ocular disease, particularly glaucoma. The apparatus consists of a locating device to locate Schlemm's Canal within the anterior portion of the eye and a surgical tool to access the canal for treatment. The apparatus allows for guided, minimally invasive surgical access to Schlemm's Canal to enable surgical procedures to be performed on the canal and trabecular meshwork to reduce intraocular pressure. The apparatus may also deliver devices or substances to Schlemm's Canal in the treatment of glaucoma.

64 Claims, 3 Drawing Sheets

TREATMENT OF OCULAR DISEASE

CROSS REFERENCE TO OTHER APPLICATIONS

This application is a divisional of U.S. Utility application Ser. No. 09/735,408, filed Dec. 11, 2000, now abandoned which claims benefit of U.S. Provisional Patent Application 60/172,693, filed Dec. 10, 1999, the specifications of which are hereby incorporated by reference in their entirety.

FIELD OF THE INVENTION

The present invention is directed to methods and apparatus for minimally invasive ocular surgery procedures and, more particularly, to the treatment of glaucoma.

BACKGROUND OF THE INVENTION

The anterior chamber of the eye is filled with a fluid known as aqueous humor. This fluid is produced by the ciliary body located adjacent to the lens. The fluid flows around the lens, through the trabecular meshwork and into an anatomical conduit, the sinus venosus sclerae, also known as Schlemm's Canal. The fluid is then expelled from the canal to the episcleral veins. In the disease state known as narrow or open angle glaucoma, the flow through the trabecular meshwork is reduced, thereby causing increased intraocular pressure, which can lead to degradation of the optic nerve and blindness. The outflow of the trabecular meshwork is typically blocked by structural or cellular debris, which is primarily age related. Various methods have been tried and used to lower the intraoptic pressure in the management of glaucoma.

Standard medical treatment for glaucoma involves topically applied drugs, including beta blockers, such as Timoptic, alpha adrenergic agonists and prostaglandin analogues. The goal of these drugs is to dilate the flow tracts in the trabecular meshwork thereby increasing flow, or to reduce the production of aqueous humor by the ciliary body. The success rate of drug treatment can range widely due to variabilities in patient response and drug side effects. These drugs are primarily delivered via drops applied directly to the eye one or two times per day. These medical treatments must also take into account patient compliance and the high cost of the drugs over time.

Surgical treatment for glaucoma has been evolving over the past two decades and includes trabeculostomy, laser trabeculoplasty, implantable shunts and viscocanalostomy. Trabeculostomy and laser trebeculoplasty involves opening or creating larger channels through the trabecular meshwork, either by surgical dissection or laser ablation of the tissues. Although effective for a short period, long term follow-up of these treatments shows marked increases in intraocular pressure and therefore low success rates. Implantable shunts, which carry the aqueous humor from the anterior chamber directly to the sclera, require precise surgical implantation and are primarily used as a last resort when all other treatment fails. Typical such devices are disclosed by Brown, et al. in U.S. Pat. No. 5,743,868 and by Wandel in U.S. Pat. No. 5,807,302. The use of shunts also involves increased surgical complications, such as infection, blebs (fluid pockets forming in the sclera at the outflow of the shunt) and blockage of the shunt over time.

A recently developed surgical treatment is known as viscocanalostomy. The procedure involves surgically opening a flap of the sclera and dissecting down to de-roof Schlemm's Canal to increase aqueous humor drainage. A high viscosity viscoelastic material is injected into the canal to dilate it, and may act to open the trabecular meshwork from the canalicular space. The viscoelastic material also acts as a fibrosis inhibitor, reducing the influx of fibroblastic cells from the healing response, which would negate the effects of the procedure by blocking fluid flow. Stegmann, et al. in U.S. Pat. No. 5,486,165 disclose a microcannula designed for delivery of substances to Schlemm's Canal during this procedure. In EP 089847A2, Grieshaber, et al. disclose an improvement to the Stegmann apparatus to deliver substances or stents for maintaining the passage of fluid in the canal. Both of these prior art citations are directed at the surgical case. While the procedure appears promising for the treatment of glaucoma, considerable training and skill is required of the practitioner. The procedure requires the precise dissection of the scleral layers and delicate manipulation of the canal, and therefore carries the concomitant risks of ocular surgery, such as infection, hypotony and endophthalmitis.

Imaging of the structure of the eye has been accomplished by various means. Ultrasound imaging is routinely used in the management of ocular disease, and such ultrasound scanners are available commercially. Ultrasound scanners normally operate in the frequency range of 10-20 MHz. The resolution at these frequencies is insufficient to provide tissue discrimination of fine structures associated with the anterior chamber such as Schlemm's Canal. Recently, higher frequency imaging systems have been developed as ultrasound biomicroscopes, e.g. P40 UBM, Paradigm Medical Industries, Salt Lake City, Utah. These systems provide imaging in the range of 40-60 MHz and are able to image the fine structure of tissues. High resolution ultrasound imaging of tissues with high frequency is also used in intravascular ultrasound (IVUS) catheters, used for the detection and characterization of vascular disease. Thomas, et al. in U.S. Pat. No. 4,911,170 disclose such a high frequency ultrasonic imaging catheter.

The combination of imaging and percutaneously introduced surgical tools has the potential to convert invasive surgical procedures into rapid minimally invasive methods. For example, image guided biopsy of breast lesions is routinely performed as an alternative to surgical dissection with advantages in reduced surgical time, patient trauma, and infection risk. Guidance under X-ray or ultrasound is used to locate a lesion and then advance a biopsy needle to the site. Many different approaches have been made to attach a biopsy needle to an ultrasound transducer to guide the biopsy needed to the general area that is being imaged. Miller, et al. in U.S. Pat. No. 5,758,650 and Park et al. in U.S. Pat. No. 5,924,992 disclose typical such devices. The prior art is directed at needle guides which are attached to any transducer and are capable of guiding biopsy needles to the target site. These needle guides are disposed at a narrow angle with respect to the transducer axis and therefore are not able to target sites that are directly under the transducer face with adequate accuracy as is required in the case of ophthalmic surgery.

The following references and all other references referred to herein are hereby incorporated by reference in their entirety:

Patent References

U.S. Pat. No. 6,142,990 2000 Burk Medical apparatus, especially for reducing intraocular pressure U.S. Pat. No. 6,007,511 1999 Prywes Shunt valve and therapeutic delivery system for treatment of glaucoma and methods and apparatus for its installation U.S. Pat. No. 6,004,318 1999 Garito, et al. Electrosurgical electrode for treating glaucoma U.S. Pat. No. 6,004,302 1999 Brierley Cannula U.S. Pat. No. 6,001,128 1999 Graff, et al. Materials for use in glaucoma filtration devices
U.S. Pat. No. 5,968,058 1999 Richeter, et al. Device for and method of implanting an intraocular implant
U.S. Pat. No. 5,941,889 1999 Cermak Multiple angle disposable needle guide system
U.S. Pat. No. 5,928,219 1999 Friend et al Fail-safe needle guide mount for ultrasonic probes
U.S. Pat. No. 5,924,992 1999 Park, et al Semi-compliant needle guide for use with ultrasound transducers
U.S. Pat. No. 5,893,837 1999 Eagles, et al Glaucoma drain implanting device and method
U.S. Pat. No. 5,879,319 1999 Pynson, et al Sclerotomy implant
U.S. Pat. No. 5,807,302 1998 Wandel Treatment of glaucoma
U.S. Pat. No. 5,785,674 1998 Mateen Device and method for treating glaucoma
U.S. Pat. No. 5,776,068 1998 Silverman, et al Ultrasonic scanning of the eye using a stationary transducer
U.S. Pat. No. 5,758,650 1998 Miller, et al. Universal needle guide for ulrasonic transducers
U.S. Pat. No. 5,752,928 1998 de Roulhac, et al Glaucoma pressure regulator
U.S. Pat. No. 5,743,868 1998 Brown, et al Corneal pressure-regulating implant device
U.S. Pat. No. 5,713,844 1998 Peyman Device and method for regulating intraocular pressure
U.S. Pat. No. 5,626,559 1997 Solomon Ophthalmic device for draining excess intraocular fluid
U.S. Pat. No. 5,626,558 1997 Suson Adjustable flow rate glaucoma shunt and method of using same
U.S. Pat. No. 5,623,931 1997 Wung, et al Needle guide for use with ultrasound imaging systems
U.S. Pat. No. 5,562,693 1996 Devlin et al. Cutting blade assembly for a surgical scissors
U.S. Pat. No. 5,522,829 1996 Michalos Surgical cutting instrument
U.S. Pat. No. 5,486,165 1996 Stegmann Method and appliance for maintaining the natural intraocular pressure
U.S. Pat. No. 5,370,607 1994 Memmen Glaucoma implant device and method for implanting same
U.S. Pat. No. 5,360,399 1994 Stegmann Method and apparatus for maintaining the natural intraocular pressure.
U.S. Pat. No. 5,331,962 1994 Coleman, et al Ultrasound system for corneal biometry
U.S. Pat. No. 5,293,871 1994 Reinstein, et al System for ultrasonically determining corneal layer thickness and shape
U.S. Pat. No. 5,290,302 1994 Pericic Surgical instrument
U.S. Pat. No. 5,217,465 1993 Steppe Flexible and steerable aspiration tip for microsurgery
U.S. Pat. No. 5,092,837 1992 Ritch, et al Method for the treatment of glaucoma
U.S. Pat. No. 4,968,296 1990 Ritch, et al Transscleral drainage implant device for the treatment of glaucoma
U.S. Pat. No. 4,940,468 1990 Petillo Apparatus for microsurgery
U.S. Pat. No. 4,934,370 1990 Campbell Pinhole focused optics for locating visual axis of the eye for ultrasonic interior measurement.
U.S. Pat. No. 4,911,170 1990 Thomas, et al. High frequency focused ultrasonic transducer for invasive tissue characterization
U.S. Pat. No. 4,484,569 1984 Driller, et al Ultrasonic diagnostic and therapeutic transducer assembly and method for using
U.S. Pat. No. 4,428,746 1984 Mendez Glaucoma treatment device
U.S. Pat. No. 4,414,974 1983 Dotson, et al Microsurgical knife
EP 0973465A 2000 Feingold, et al A glaucoma drain implanting device and method
EP 0914169A 1999 Graff, et al Materials for use in glaucoma filtration devices
EP 0898947 1998 Grieshaber, et al Method and apparatus to improve the outflow of aqueous humor from the eye
EP 0881055A 1998 Gabriel, et al Method and apparatus for implanting an artificial meshwork in glaucoma surgery
EP 0532654 1996 Baerveldt, et al Glaucoma Implant
WO 00/67687 2000 Junger, et al Device for treating glaucoma of the eye
WO 00/64511 2000 Williams et al A glaucoma shunt and a method of making and surgically implanting the same
WO 00/64393 2000 Warren Shunt device and method for treating glaucoma
WO 00/64391 2000 Warren Stent device and method for treating glaucoma
WO 00/64390 2000 Warren Inflatable device and method for treating glaucoma
WO 00/64389 2000 Warren Trabeculotomy device and method for treating gluacoma
WO 00/50040 2000 Stjernschantz et al Method and composition for prevention of scar formulation in glaucoma filtration bleb and drainage fistula
WO 00/06223 1999 Niger, et al Sutures implantable device and a method for treatment of glaucoma
WO 99/66862 1999 Adelberg, et al Non-invasively adjustable valve implant for the drainage of aqueous humor in glaucoma
WO 99/66871 1999 Cruz et al Intraocular pressure regulating valve
WO 99/38470 1999 Soltanpour Method and apparatus for controlling intraocular pressure
WO 99/26567 1999 Yaron, et al Flow regulating implant, method of manufacturing, and delivery device.
WO 98/50092 1998 Baerveldt Method and apparatus for inserting a glaucoma implant in an anterior and posterior segment of the eye.
WO 98/30181 1998 Allan, et al Device for use in the eye
WO 97/21406 1997 Nordquist, et al Apparatus for lowering the intraocular pressure of an eye
Non-Patent References
Carassa R G, Betin P, et al, "Viscocanalostomy: a pilot study", Eur J Opthalmol, April-June 1998, 8(2):57-61.Deng, C. X. et al. "Imaging and Spectrum Analysis of Contrast Agents in the In-vivo Rabbit Eye Using Very-High-Frequency Ultrasound". Ultrasound in Medicine and Biology, 1998, Vol. 24, No. 3, pp. 383-394.
Hyong PF, van Beek LM, "Pharmacological therapy for glaucoma: a review", Drugs, March 2000, 50(3):411-34.
Lieb, W. E., M. D. "Color Doppler Imaging of the Eye and Orbit". Imaging in Opthalmology I. Radiologic Clinics of North America. November, 1998, Vol. 36, No. 6, pp. 1059-1071.
Lundgren B O, Scampini G, Wickstrom K, Stegman R, "Histopathological evaluation in monkey eyes of the viscocanalostomy technique", Abstract 438-B438, 2000 ARVO meeting, published in IOVS, Mar. 15, 2000, No 4, pg S83.
Obstbaum, S., M. D. et al. "Cutting Edge Glaucoma Surgery: Will Viscocanalostomy Light the Way?". Supplement to the Review of Opthalmology, September 1999.
Olsson, M., Campbell, K., Turnbull, D. H. "Specifications of Mouse Telencephalic and Mid-Hindbrain Progenitors Following Heterotopic Ultrasound-Guided Embryonic Transplantation". Neuron, October, 1997, Vol 19, pp. 761-772.

Pavlin, C. J., M D, Foster, F. S. PhD. "Ultrasound Biomicroscopy. High Frequency Ultrasound Imaging of the Eye at Microscopic Resolution". Imaging in Opthalmology I. Radiologic Clinics of North America. November, 1998, Vol. 36, No. 6, pp 1047-1058.

Smith B A, Johnstone M A, "Effects of viscocanalostomy on the histology of Schlemm's Canal in primate eyes", Abstract 3072-B170, 2000 ARVO meeting, published in IOVS, Mar. 15, 2000, Vol 41, No 4, pg S578.

Stegmann R, Pienaar A, Miller D, "Viscocanalostomy for open-angle glaucoma in black African patients", J Cataract Refract Surg, March 1999; 25(3):316-22.

Welsh, N. H., FRCS et al. "The "Deroofing" of Schlemm's Canal in Patients with Open-Angle Glaucoma Through Placement of a Collagen Drainage Device". Ophthalmic Surgery and Lasers, March 1998, Vol. 29, No. 3, pp 216-226.

SUMMARY OF THE INVENTION

In a first aspect, the present invention provides non-invasive locating device of determining the location of Schlemm's Canal in the eye. Using such means to indicate the location of the canalicular space, minimally invasive procedures can then be performed using surgical devices as specified herein. Such surgical devices can be used for injecting or inserting of active or passive substances or constructs into the canal for the treatment of glaucoma. Locating devices suitable for use in the present invention include ultrasonic and optical locating or imaging devices.

In a second aspect, the present invention provides minimally invasive surgical devices coupled to the locating device to access Schlemm's Canal in the eye for the delivery of treatments for ocular disease. These devices include microcannulas with appropriate geometry and mechanical properties to access Schlemm's Canal through the scleral tissues under guidance of the locating device. The microcannulas may be used to deliver a surgical viscoelastic material to expand the canal, or may incorporate mechanical expansion means to expand the canal directly. Alternatively, microsurgical tools may be used with the microcannula to perform surgery on the trabecular meshwork to reduce intraocular pressure via Schlemm's Canal.

In a third aspect, the present invention describes certain substances and constructs to be delivered to the eye via minimally invasive access. These materials are directed to the treatment of ocular disease and include, but are not limited to, stents, microparticles, and drug delivery materials.

The present invention is directed at a novel minimally invasive treatment for ocular disease, and glaucoma in particular. Beyond medicinal treatments, the prior art is directed to the surgical treatment of glaucoma. Such surgical intervention requires highly trained skills and presents the risks associated with ocular surgery. The present invention is directed at an apparatus and method to localize a treatment site in the eye, advance a minimally invasive surgical device to the site and deliver substances, constructs or microsurgical tools for the treatment of the disease state.

In accordance with the method of the invention, there is provided an apparatus to detect the location of anatomical features such as Schlemm's Canal. The locating device may operate by ultrasound examination, using either an imaging or non-imaging ultrasound system. The scleral tissue containing Schlemm's Canal may be examined non-invasively with ultrasound by placing an appropriate transducer on the surface of the sclera. The target location of the canal may be identified by discrimination of the ultrasound signal transmitted and received from the transducer. Characterization of the received ultrasound signal can be used to identify differences in tissue density presented by Schlemm's Canal and analysis modes such as Doppler may detect the flow of aqueous humor within the canal. The ultrasound signals would ideally span a region of the sclera to allow either a video image of the region to be displayed or to provide guiding signals from the transducer assembly to guide the surgical tool to the site. In a preferred embodiment, a surgical tool would be coupled to the transducer assembly, incorporating means to accurately advance the tool to the target tissue space identified by ultrasound.

Preferably, the ultrasound system utilizes a high frequency transducer in order to have the resolution needed for detection of the canal, which can range from 20 to 150 microns in diameter. Ultrasound frequencies in the range of 10 to 200 MHz are preferred. The ultrasound system may use various operating or analysis modalities, such as Doppler or harmonic methods to discriminate the target. In a preferred embodiment, the ultrasound system utilizes a transducer constructed from a piezoelectric material, for example a thin piezoelectric polymer film such as polyvinylidene difluoride (PVDF), and configured to provide a broad-band focused image at 40-150 Mhz, coupled to a computer system for the transmission, reception and processing of the imaging data and display of the resultant image. The ultrasound detection may be further enhanced by using a contrast agent as a tracer for the aqueous humor. In the case of ultrasound, gas is typically used as a contrast agent, usually air, nitrogen or high molecular weight fluorocarbon gases. Gas can be delivered in its gaseous state, in the form of a low boiling-point physiologically compatible liquid, or entrapped in microspheres. The gas or microspheres may be delivered to Schlemm's Canal by intra-corneal injection. Alternatively, retrograde injection into the episcleral veins of the eye may be accomplished.

In a second embodiment, optical imaging is used to locate the canal. Fluorescein is a fluorescent tracer commonly used in ophthalmic procedures. Fluorescein may be administered to the eye and time allowed for the tracer to traverse the trabecular meshwork and into the canal. Using a high sensitivity photodetector, coupled with an illuminating source, the tracer in the canal can be visualized. Alternatively, a high intensity light source may be used to locate the canal due to the coloration differences in the surrounding structure. Furthermore, ultra-high sensitivity infrared detection may be used to detect any temperature difference between the fluid-filled canal and the surrounding scleral tissues, with our without the use of a tracer compound. Other optical methods such as optically coherent tomography or confocal imaging may also be utilized in similar fashion.

The locating device may consist of a base or console unit with a display and system controls, coupled to a handpiece which is used to locate the target site, or in the case of non-imaging means, may consist solely of a handpiece which contains the necessary components to effect the procedure. The handpiece may be mounted on an armature apparatus that is connected to the base unit or may be attached to the operative surface with a clamping device. The handpiece consists of a locating device with a surgical access device coupled to the locating device in such a manner as to allow the surgical device to advance into the target site. The handpiece may comprise a single unit containing both devices, or the apparatus of the surgical device may be made attachable and detachable from the handpiece of the locating device. In the preferred embodiment, a single unit handpiece is constructed such that the surgical device is disposed so as to enter the tissues tangentially to Schlemm's Canal, whilst an imaging means is aligned along the axis of the canal in order to visualize the procedure. The surgical device is preferably held at an angle between 0 and 40 degrees from the axis of the canal. An adjusting mechanism may be incorporated into the surgical access device to fine-tune the depth of penetration. In another embodiment the surgical device is disposed coaxially with the locating device. The surgical device may be located centrally between two imaging transducers, with the image from the dual transducers being combined by the image processing system.

The handpiece incorporating the locating device and the surgical device presents a suitable contacting surface to the eye. A slight curvature of the tissue contacting surfaces of the apparatus approximating the radius of the eye aids mechanical stability for the precise surgical placement of the surgical device. The contacting surfaces may also be modified to hold or deliver a coupling fluid or gel to aid energy transfer for the locating device.

The invention is further directed to a novel surgical access device to enter the target site using minimally invasive techniques. The surgical access device is coupled to the locating device and consists of a mechanism to advance a microcannula or other surgical device into the target space while maintaining the operative position via the locating device. The surgical access device comprises a microcannula, axially disposed in a retaining means, together with the mechanism to advance the microcannula into the target. In practice, the locating device is used to find Schlemm's Canal and the microcannula is advanced into the canal. If an imaging system is used to target the site, then the advancement of the microcannula can progress under image guidance. The microcannula is suitably dimensioned and shaped so as to be able to penetrate through the tissue of the sclera, to enter the canalicular space and to allow advancement into Schlemm's Canal with minimal risk of trauma to adjacent tissues. The microcannula may incorporate a curvature approximating the 12-14 mm radius curvature of Schlemm's Canal. A cutting tip to penetrate the scleral tissues may be incorporated into the microcannula tip or separately in the positioning mechanism for the surgical device, for example in a guiding outer sheath incorporating a centrally disposed obturator with a cutting tip. In one embodiment, the microcannula is advanced using manual mechanical means such as a screw mechanism or rack and pinion mechanism. In another embodiment, the microcannula is advanced using powered means such as pneumatic, hydraulic or electro-mechanical propulsion. In another embodiment, the microcannula is advanced using powered means and under guidance control by the imaging system. The microcannula may be used to deliver drugs, or materials, such as viscoelastics or other such substances, imaging fibers or microsurgical tools.

The invention is further directed to constructs and microsurgical tools that are delivered into the target location by the access device in order to accomplish the treatment desired. Constructs such as biodegradable stents, microparticles and drug delivery materials are herein disclosed. Microsurgical tools such as dilators, cutters and fiber optics are included.

DETAILED DESCRIPTION OF THE INVENTION

Figure 1:
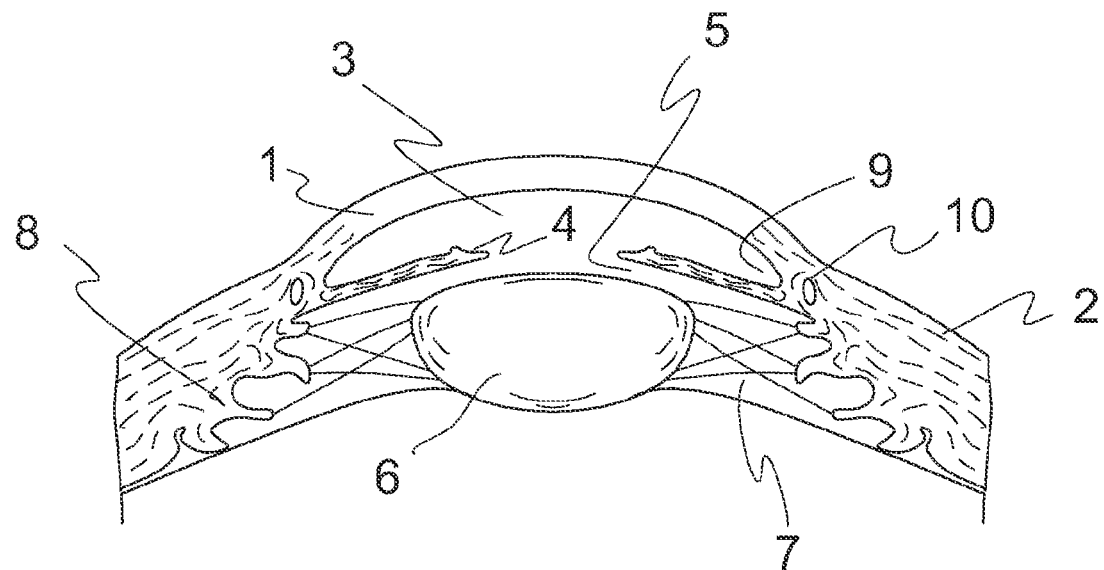
FIG. 1 shows a cross-sectional view of the anterior portion of the eye.

FIG. 1 shows a cross-sectional view of the anterior portion of the eye, detailing the structures therein. The cornea 1 is the transparent section at the most anterior part of the structure. Adjacent to the cornea 1 is the opaque sclera 2 which comprises the bulk of the outer surface of the eyeball. Beneath the cornea 1 lies the anterior chamber 3 which is filled with aqueous humor. The iris 4 is suspended above the posterior chamber 5 and controls the amount of light entering the lens 6. The lens 6 is held in place by the suspensory ligaments 7. The aqueous humor is produced by the ciliary body 8, and the fluid flows around the lens 6, through the posterior chamber 5 and into the anterior chamber 3. The fluid then flows through the trabecular meshwork 9 and into Schlemm's Canal 10. The fluid is then expelled through a capillary network to the episcleral veins.

Figure 2:
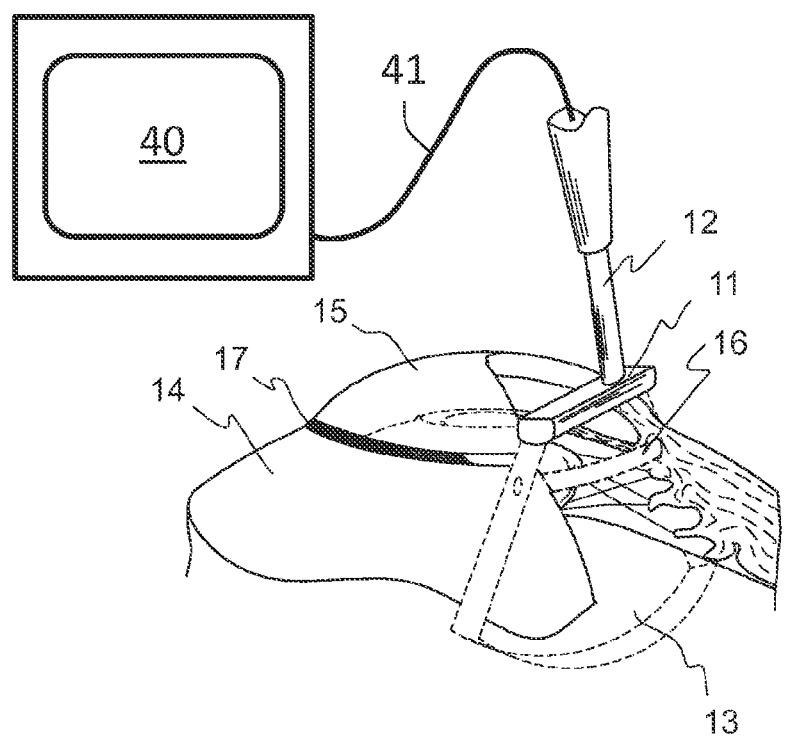
FIG. 2 shows a sectional view of the anterior portion of the eye with an ultrasound transducer or optical detector scanning to determine the location of Schlemm's Canal.

FIG. 2 shows a locating device in accordance with the apparatus of the present invention. The locating device may be imaging or non-imaging. In a preferred embodiment, the locating device includes a sector scanning ultrasound transducer or optical detector 11, mounted at right angles to a handpiece 12, through which are carried the connecting wires 41 from a computer or image processing system with a display device 40. The imaging plane 13 of the transducer 11, scans for the location of Schlemm's Canal 16. The transducer 11 is placed on the surface of the sclera 14 and scanned radially from the cornea 15 and limbus 17 to determine the accurate location of Schlemm's Canal 16. The tissue contacting surface of the transducer 11 is suitably curved to be able to smoothly scan the surface of the sclera. The surgical device is not illustrated in this figure.

Figure 3:
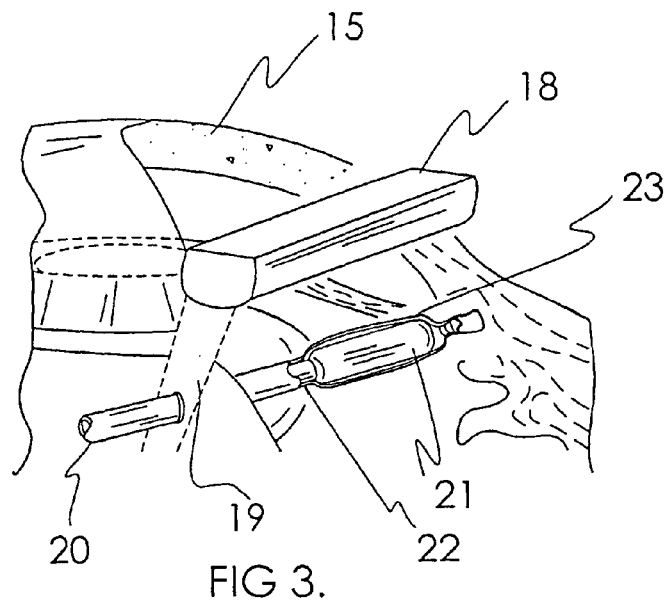
FIG. 3 shows a sectional view of the anterior portion of the eye with an ultrasound transducer or optical detector imaging a dilating mechanism that has been advanced into Schlemm's Canal.

FIG. 3 shows a locating device and a minimally invasive microsurgical device in accordance with the apparatus of the present invention. A sector scanning ultrasound transducer or optical detector 18 is shown with its imaging plane 19 located over Schlemm's Canal 22 and imaging a microcannula 20 introduced into the canal 22. The distal tip of the microsurgical device is comprised of an elastomeric dilating balloon 21. The balloon 21 may be incorporated directly into the distal end of the microcannula 20, or a separate device having the balloon 21 mounted thereon may be introduced through the microcannula 20. The balloon 21 is shown dilating the canal 22 from its pre-surgical state 22 to an expanded state 23. The microcannula is advanced along the canal, dilating successive segments.

Figure 4:
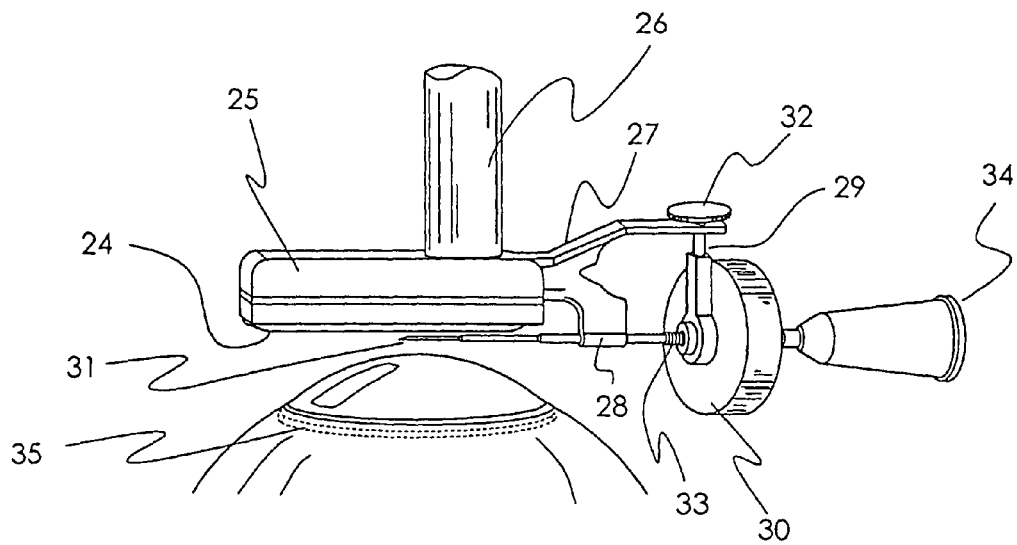
FIG. 4 shows a side elevation view of a coupled ultrasound imaging transducer or optical detector and a microcannula surgical device.

FIG. 4 shows a side elevation of an embodiment of the apparatus of the present invention incorporating a locating device, a minimally invasive microsurgical device and a surgical access device for guiding the microsurgical device in relation to the locating device. An ultrasound sector scanning transducer or optical detector 24 is disposed on the bottom side of a transducer housing 25, which is attached to a handle 26. The transducer housing 25 extends axially to form a cantilever beam 27. The cantilever beam 27 comprises a guiding sleeve 28, an angle adjustment mechanism 29 and a thumbwheel mechanism 30 for advancing the microcannula 31. The depth of penetration of the microcannula 31 is controlled with the angle adjustment knob 32 and the axial motion of the microcannula 31 is controlled by the thumbwheel 30 advancing a lead screw 33 on the microcannula 31. The proximal end of the microcannula 31 is comprised of a female Luer fitting 34 for attachment of a syringe or the like. In use, Schlemm's Canal 35 is located using the transducer 24, and the microcannula 31 is advanced through the sclera into the canal.

Figure 5:
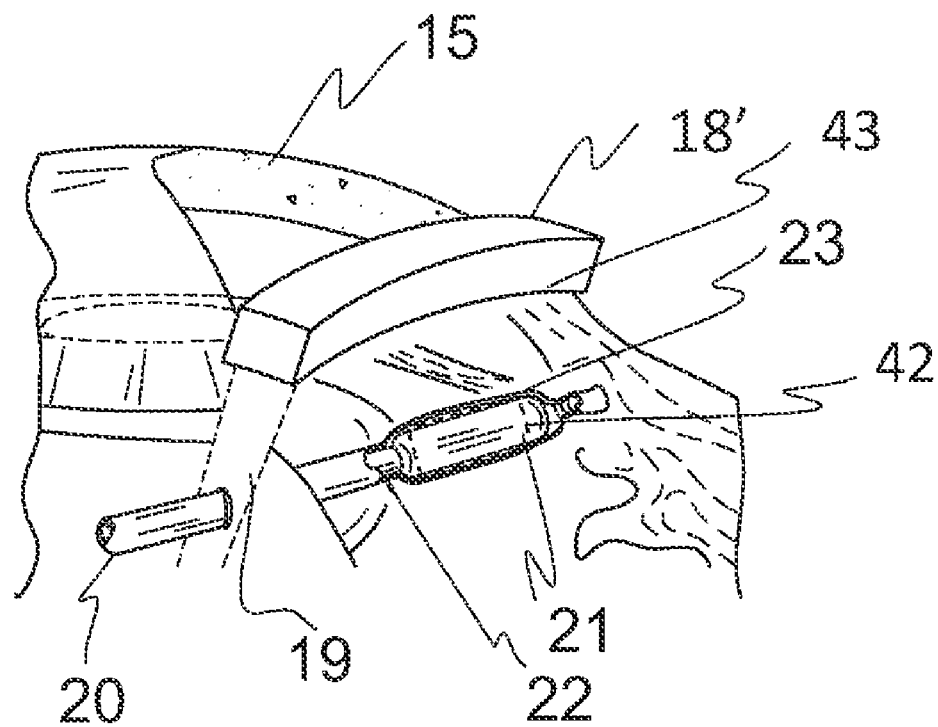
FIG. 5 shows a transducer with a curved tissue contacting surface to accommodate the curvature of the eye.

FIG. 5 shows a transducer 18' with a curved tissue contacting surface 43 to accommodate the curvature of the eye. FIG. 5 further illustrates an implant 42, such as a stent, microparticles, and/or drug delivery materials, configured for implantation by the microsurgical device into Schlemm's Canal to maintain flow of aqueous humor.

Figure 6:
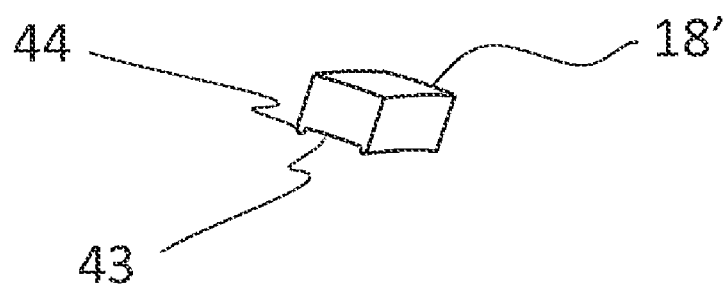
FIG. 6 is a cutaway drawing of the transducer of FIG. 5 showing a raised ridge around the circumference of the curved tissue contacting surface.

FIG. 6 is a cutaway drawing of the transducer 18' of FIG. 5 showing a raised ridge 44 around the circumference of the curved tissue contacting surface 43 to keep coupling gel in place between the tissue contacting surface 43 and the surface of the patient's eye.

The following are given as examples of the method of the present invention for minimally invasive ocular surgery procedures and particularly for treatment of glaucoma. These exemplary descriptions of the method may be understood by reference to the drawing figures and the preceding description of the apparatus of the present invention.

EXAMPLE 1

An experiment was performed to determine the target resolution of high frequency ultrasound. An ultrasound phantom was prepared to emulate micro channels of various diameters. The phantom was prepared by placing stainless steel tubing (Small Parts, Inc. Miami Lakes, Fla.) of various diameters across a standard 80 mm styrene petri dish, spaced 10 mm apart. A 10% solution of gelatin, 250 bloom (Woburn, Edible Pork Skin Gelatin) was prepared by heating gelatin powder in distilled water until fully in solution. The gelatin solution was poured into the petri dish until the tubes were covered to a depth of approximately 1 mm. The gelatin was allowed to solidify by cooling and subsequently the tubes were withdrawn from the petri dish leaving open channels of various diameters. Channel diameters of 110, 150, 205, 230 and 255 microns were created in this manner. Luer hub tubing connectors were bonded to the ends of the channels to allow for injection of fluids in the channels.

The experiment was performed in an Ultrasound Biomicroscope (UBM, Humphreys, Inc., Model PB-40) which has a transducer frequency of 50 Mhz. The UBM consisted of a single crystal imaging system with the transducer mounted on a scan translator operating at 8 Hz. The ultrasound phantom was placed on a flat surface, and a small amount of water was placed on top to act as a coupling agent between the transducer and the phantom. The phantom was scanned using B-mode imaging. The channels were imaged in axial and perpendicular directions and at various focal depths. The channels were also imaged with both air and water in the lumen. In all cases, the channels were able to be imaged with the UBM. Using the caliper measurement function of the UBM, all the channel images were measured, with good correspondence between the actual channel dimension and the measured image dimension. The 50 Mhz system was capable of target resolution and discrimination for the complete range of phantom channel diameters simulating the ultrasound detection of Schlemm's Canal.

EXAMPLE 2

A unitary system is constructed comprised of a focused ultrasound transducer mounted at a right angle to the handpiece and an injection system coupled to the handpiece and whose axis is disposed in the same plane as the scan wedge of the transducer. The transducer is connected to a hardware system comprised of a signal generator, signal receiver, an image processing system and a display. The ultrasound imaging system is used to determine the location of Schlemm's Canal. The ultrasound transducer operating between 40 and 150 MHz transmit frequency is used to image the episcleral tissues near Schlemm's Canal. Preferably, the ultrasound system has an axial and lateral resolution of at least 60 microns for imaging of fine structures and is capable of discriminating Schlemm's Canal, whose central axis is disposed between 450-600 microns beneath the scleral surface. The tissue contacting surface of the transducer is curved to accommodate the curvature of the eye and a slight raised ridge around the circumference of the face keeps coupling gel in place. An ultrasonic coupling gel is placed on the eye of the subject and then the transducer is placed in contact with the eye. A scan is made of the sclera, with the transducer scan plane tangential to the limbus, and proceeding radially from the limbus until the structure of Schlemm's Canal is seen on the ultrasound image or detected from reflected ultrasound characteristics of the canal.

An injection system is comprised of a microcannula, disposed within a guiding means. The microcannula has a distal diameter between 50 and 150 microns and the distal end is beveled so as to allow tissue penetration. The injection system is disposed at a 90 degree angle to the handpiece, and as such is in the plane of Schlemm's Canal to affect tangential access. The angle of the injection system is capable of being tuned to a fine degree by an angle adjusting screw mechanism disposed at right angles to the axis of advancement. The proximal end of the microcannula is fabricated with a fine pitch screw thread and a thumbwheel mechanism in the guiding means allows controlled advancement of the microcannula. The injection system is accurately aligned to the ultrasound scan plane so as to allow the microcannula to hit a target point within the canal.

Under ultrasound or visual guidance, the microcannula is advanced through the epi-scleral tissue and into the canal. The proper access of the canal may be seen by the positioning of the microcannula tip in reference to the ultrasound image, and confirmed by the flashback of aqueous humor into the microcannula or by fluid flow identified by the ultrasound characteristics such as Doppler analysis. Once properly positioned, a compliant dilating mechanism is disposed through the microcannula and into the canal. The dilating mechanism has an elastomeric expandable distal end, which is inflated via a syringe attached to the proximal end. The dilating mechanism is alternately expanded, deflated and then advanced to another portion of the canal. The dilating portion is constructed to achieve a final outer diameter between 200 and 300 microns and is used to expand the canal and to thereby open up the trabecular meshwork to allow increased aqueous humor flow.

EXAMPLE 3

A microsurgical system as described in Example 2 is adapted for introduction of the microcannula by mechanized means under guidance from the processed ultrasound signal. The control system is designed to provide introduction and redirection of the microcannula as determined by the known location of the microcannula tip relative to the estimated location of Schlemm's Canal from the ultrasound imaging and analysis system.

EXAMPLE 4

An ultrasound contrast agent may be pre-delivered to the region to aid detection of Schlemm's Canal. The ultrasound contrast agent may comprise stabilized or encapsulated gas bubbles of a physiologically compatible gas. Alternatively, the gaseous ultrasound contrast agent may be derived as a low temperature boiling-point fluorocarbon emulsion or liquid that has been injected. The gas can be injected into the anterior chamber of the eye, near the trabecular meshwork to flow into Schlemm's Canal. Alternatively, the gas is delivered via retrograde injection into the episcleral veins. A small stab wound is made into the anterior chamber in order to partially drain the aqueous humor. This sets up a retrograde flow that allows venous blood to enter into Schlemm's Canal. By depositing the gas into the episcleral vein, the reverse flow carries the gas into the canal. The presence of the gas will allow easy detection with an ultrasound scanner by enhancing the ultrasound reflectivity of the canal.

EXAMPLE 5

A non-imaging ultrasound guidance system is utilized to locate Schlemm's Canal. A handheld ultrasound tool with a transducer tip and integrated microcannula apparatus is used to probe the sclera, where the ultrasound tool provides threshold discrimination of tissue density at a depth of 0.3 to 4 mm in depth. A signaling light, audio output or other signaling means on the ultrasound tool is triggered upon locating the transducer tip over Schlemm's Canal. A mechanical advancement device for the microcannula is activated, advancing the distal tip of the microcannula to the appropriate depth identified by the ultrasound detection system.

EXAMPLE 6

A 1 mg/ml solution of sodium fluorescein was prepared in physiological buffer to act as an optical marker. An ex-vivo porcine eye was dissected in the scleral region to an approximately 1 mm depth and a 30 gauge needle used to create a short needle tract of approximately 1 cm in length, 0.5 mm from the surface to simulate Schlemm's Canal of the eye found in humans and primates. The tract was filled with the sodium fluorescein solution as an optical marker. A medium intensity ultraviolet light, (UVP, 366 nm) was used to visualize the optical marker from the surface of sclera, demonstrating clear visualization of the simulated canal for microcannulation either manually or with computer guidance.

EXAMPLE 7

In advance of treatment, fluorescein tracer is administered to the eye of the patient. After a suitable period has elapsed, such that the fluorescein has had time to enter Schlemm's Canal, a high sensitivity photodetector is used to detect the fluorescence in the canal. The detector apparatus is moved radially outward from the limbus until detection of the canal is achieved. The apparatus consists of a focused ultraviolet light source of output wavelength at the peak fluorescence absorption wavelength of the tracer and a highly sensitive photodetector effective near the peak emission wavelength of fluorescein. Within the detector handpiece, an indicator light illuminates or a buzzer sounds when the fluorescein is detected. A mechanical guidance device for the microcannula is attached to the handpiece, allowing the microcannula to be advanced into Schlemm's Canal upon signals from the optical detection system.

EXAMPLE 6

Schlemm's Canal is located using means similar to Examples 1-4. An access device is attached to the handpiece of the locating device. The device consists of a microcannula, slidably disposed in a sheath, with means for advancing the microcannula into the injection site. The microcannula has a distal dimension between 50 and 150 microns diameter and a distal tip that is beveled so as to have a tissue penetrating point. The microcannula is advanced into a target site, such as Schlemm's Canal. If an imaging means is used, then the location of the microcannula tip is confirmed during placement by the imaging system. The microcannula is used to deliver a construct such as an expandable stent into the canal. The stent may comprise permanent or biodegradable materials. The stent may be in the form of a solid tube structure with openings in the side to allow fluid flow, a tube structure fabricated from a mesh or a matrix or sponge-like cylinder.

EXAMPLE 8

After locating Schlemm's Canal by minimally invasive means, a microcannula guided by the locating device is inserted into the canal. The microcannula is used to deliver a viscoelastic material to the canal. The viscoelastic material may comprise permanent or biodegradable materials. In one particularly preferred embodiment, the viscoelastic material is comprised of sodium hyaluronate.

EXAMPLE 9

After locating Schlemm's Canal by minimally invasive means, a microcannula guided by the locating device is inserted into the canal to allow access of microsurgery tools for direct surgical intervention on the trabecular meshwork. The tools may include scissors, cutters, dilators or other such devices. Alternatively, the microcannula may be used to introduce fiber optic or laser devices to perform imaging or phototherapeutic procedures.

EXAMPLE 10

After locating Schlemm's Canal by minimally invasive means, a microcannula guided by the locating device is inserted into the canal to deliver microspheres to the canal. The microspheres may comprise permanent or degradable materials. The microspheres act as a dilation mechanism for the canal, while the interstices between the microspheres allow fluid flow through the canal.

EXAMPLE 11

After locating Schlemm's Canal by minimally invasive means, a microcannula guided by the locating device is inserted into the canal, wherein the microcannula is used to deliver a drug-containing material to the canal. The material is intended to deliver drugs suitable for the treatment of ocular disease. The drug delivery means may comprise permanent or biodegradable materials. The material may partly comprise the drug, or contain the drug within reservoirs such that the drug is released during degradation or leached out with the flow of aqueous humor through the material. The material may be in the form of an implant to provide long term drug delivery. The implant may be in the form of a solid, porous or sponge-like device.

EXAMPLE 12

After locating Schlemm's Canal by minimally invasive means, a microcannula guided by the locating device is inserted into the canal, wherein the microcannula is used to deliver microsurgical tools to areas of the eye including Descemet's window and the trabecular meshwork for increasing the flow of aqueous into Schlemm's Canal.

EXAMPLE 13

After locating Schlemm's Canal by minimally invasive means, a microcannula guided by the locating device is inserted into the canal, wherein the microcannula is used to deliver implants which increase the flow of aqueous through the trabecular meshwork and into Schlemm's Canal.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
wherein the locating device comprises an ultrasound imaging transducer; and
wherein the tissue contacting surface of the locating device is curved to approximate a curve of the exterior surface on an anterior of the patient's eye.

2. The apparatus of claim 1, further comprising an image processing system and a display device for displaying an ultrasound image of the eye produced by the ultrasound imaging transducer of the locating device, the ultrasound image of the eye providing a visual indication of when Schlemm's Canal is located in the imaging plane of the locating device distal to the tissue contacting surface of the locating device.

3. The apparatus of claim 1, wherein the ultrasound imaging transducer operates at an ultrasound frequency of at least 10 MHz.

4. The apparatus of claim 1, wherein the ultrasound imaging transducer operates at an ultrasound frequency of at least 40 MHz.

5. The apparatus of claim 1, further comprising means to introduce an ultrasound contrast agent into the patient's aqueous humor.

6. The apparatus of claim 1, wherein the locating device further comprises an audible or visible signal to indicate when Schlemm's Canal is located in the imaging plane of the locating device distal to the tissue contacting surface of the locating device.

7. The apparatus of claim 1, wherein the locating device further comprises a raised ridge around a periphery of the tissue contacting surface.

8. The apparatus of claim 1, wherein the microsurgical device comprises a microcannula.

9. The apparatus of claim 8, wherein the microcannula incorporates a cutting tip to penetrate a sclera of the eye.

10. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
wherein the microsurgical device comprises a microcannula; and
wherein a distal portion of the microcannula is curved with a radius of approximately 12-14 mm to accommodate a curvature of Schlemm's Canal.

11. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
wherein the microsurgical device comprises a microcannula; and
wherein the microcannula has an outer diameter of less than 200 microns.

12. The apparatus of claim 11, wherein the locating device comprises an ultrasound imaging transducer.

13. The apparatus of claim 12, wherein the tissue contacting surface of the locating means is curved to approximate a curve of the exterior surface on an anterior of the patient's eye.

14. The apparatus of claim 12, wherein the tissue contacting surface of the locating device is curved to approximate a curve of the exterior surface on an anterior of the patient's eye.

15. The apparatus of claim 14, wherein the locating device comprises an optical detector.

16. The apparatus of claim 15, further comprising an image processing system and a display device for displaying an optical image of the eye produced by the optical detector of the locating device, the optical image of the eye providing a visual indication of when Schlemm's Canal is located in the imaging plane of the locating device distal to the tissue contacting surface of the locating device.

17. The apparatus of claim 15, wherein the locating device further comprises an audible or visible signal to indicate when Schlemm's Canal is located in the imaging plane of the locating device distal to the tissue contacting surface of the locating device.

18. The apparatus of claim 15, further comprising means to introduce to a fluorescent tracer into the patient's aqueous humor.

19. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
wherein the microsurgical device comprises a microcannula; and
an inflatable dilating balloon mounted on a distal end of the microcannula.

20. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
a microsurgical device comprising a microcannula;
a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device; and
a device having an inflatable dilating balloon mounted on a distal end of the device, wherein the distal end of the device is configured for insertion through the microcannula.

21. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm'Canal is located in a imaging plane that extends distally from the tissue contacting surface of the locating device;
a microsurgical device;
a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device; and
an implant configured for implantation by the microsurgical device into Schlemm's Canal to maintain flow of aqueous humor.

22. The apparatus of claim 21, wherein the implant comprises a stent.

23. The apparatus of claim 22, wherein the stent comprises a biodegradable material.

24. The apparatus of claim 21, wherein the implant comprises microparticles.

25. The apparatus of claim 24, wherein the microparticles comprise a biodegradable material.

26. The apparatus of claim 21, wherein the implant comprises microspheres.

27. The apparatus of claim 26, wherein the microspheres comprise a biodegradable material.

28. The apparatus of claim 21, wherein the implant comprises a drug releasing material.

29. The apparatus of claim 28, wherein the drug releasing material contains a drug effective in the treatment of glaucoma.

30. The apparatus of claim 21, wherein the microsurgical device comprises a microcannula slidably positioned within a guide sleeve.

31. An apparatus for treating ocular disease in a patient, the apparatus comprising:
a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
wherein the locating device comprises an optical detector; and wherein the optical detector comprises a high intensity white light illumination source.

32. An apparatus for treating ocular disease in a patient, the apparatus comprising:
  a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
  a microsurgical device;
  and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
  wherein the locating device comprises an optical detector; and
  wherein the optical detector comprises an optically coherent illumination source.

33. An apparatus for treating ocular disease in a patient, the apparatus comprising:
  a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
  a microsurgical device;
  and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
  wherein the locating device comprises an optical detector; and
  wherein the optical detector comprises a fiber optic device.

34. An apparatus for treating ocular disease in a patient, the apparatus comprising:
  a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
  a microsurgical device;
  and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
  wherein the locating device comprises an optical detector; and
  wherein the optical detector utilizes detection via visible wavelengths of light.

35. An apparatus for treating ocular disease in a patient, the apparatus comprising:
  a locating device, the locating device having a tissue contacting surface configured for contacting an exterior surface of the patient's eye, the locating device adapted for non-invasively locating Schlemm's Canal within the patient's eye and for indicating when Schlemm's Canal is located in a imaging plane that extends distally from the tissue contacting surface of the locating device;
  a microsurgical device;
  and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately parallel to the tissue contacting surface of the locating device;
  wherein the locating device comprises an optical detector; and
  wherein the optical detector utilizes detection via infrared wavelengths.

36. An apparatus for treating ocular disease in a patient, comprising:
  a handle, the handle having a longitudinal axis;
  a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;
  a microsurgical device;
  and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus;
  wherein the tissue contacting surface of the locating device is curved to approximate a curve of the exterior surface on an anterior of the patient's eye.

37. The apparatus of claim 36, wherein the locating device comprises an ultrasound imaging transducer.

38. The apparatus of claim 37, further comprising an image processing system and a display device for displaying an ultrasound image of the eye produced by the ultrasound imaging transducer of the locating device, the ultrasound image of the eye providing a visual indication of when Schlemm's Canal is located in the imaging plane of the locating device distal to the tissue contacting surface of the locating device.

39. The apparatus of claim 37, wherein the ultrasound imaging transducer operates at an ultrasound frequency of at least 10 MHz.

40. The apparatus of claim 37, wherein the ultrasound imaging transducer operates at an ultrasound frequency of at least 40 MHz.

41. The apparatus of claim 37, further comprising means to introduce an ultrasound contrast agent into the patient's aqueous humor.

42. The apparatus of claim 37, wherein the locating device further comprises an audible or visible signal to indicate when Schlemm's Canal is located in the imaging plane of the locating device distal to the tissue contacting surface of the locating device.

43. The apparatus of claim 36, wherein the locating device further comprises a raised ridge around a periphery of the tissue contacting surface.

44. The apparatus of claim 36, wherein the microsurgical device comprises a microcannula.

45. The apparatus of claim 44, wherein the microcannula incorporates a cutting tip to penetrate a sclera of the eye.

46. An apparatus for treating ocular disease in a patient, comprising:
a handle, the handle having a longitudinal axis;
a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus;
wherein the microsurgical device comprises a microcannula; and
wherein a distal portion of the microcannula is curved with a radius of approximately 12-14 mm to accommodate a curvature of Schlemm's Canal.

47. An apparatus for treating ocular disease in a patient, comprising:
a handle, the handle having a longitudinal axis;
a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;
a microsurgical device;
and a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus;
wherein the microsurgical device comprises a microcannula; and
wherein the microcannula has an outer diameter of less than 200 microns.

48. An apparatus for treating ocular disease in a patient, comprising:
a handle, the handle having a longitudinal axis;
a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;
a microsurgical device comprising a microcannula;
a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus; and
an inflatable dilating balloon mounted on a distal end of the microcannula.

49. An apparatus for treating ocular disease in a patient, comprising:
a handle, the handle having a longitudinal axis;
a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;
a microsurgical device comprising a microcannula;
a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus; and
a device having an inflatable dilating balloon mounted on a distal end of the device, wherein the distal end of the device is configured for insertion through the microcannula.

50. An apparatus for treating ocular disease in a patient, comprising:
a handle, the handle having a longitudinal axis;
a locating device, the locating device having a tissue contacting surface configured for contacting an exterior surface of the patient's eye, the locating device being coupled to the handle such that the tissue contacting surface is approximately perpendicular to the longitudinal axis of the handle, the locating device adapted for non-invasively locating Schlemm's Canal within the patient's eye and for indicating when Schlemm's Canal is located in a imaging plane that extends distally from the tissue contacting surface of the locating device;

a microsurgical device;

a surgical access device physically coupled to the locating device for guiding the microsurgical device in relation to the locating device, the surgical access device being configured to access Schlemm's Canal within the imaging plane of the locating device and to deliver the microsurgical device into Schlemm's Canal along a path spaced apart distally from the tissue contacting surface of the locating device and approximately perpendicular to the longitudinal axis of the handle of the apparatus; and an implant configured for implantation by the microsurgical device into Schlemm's Canal to maintain flow of aqueous humor.

51. The apparatus of claim 50, wherein the implant comprises a stent.

52. The apparatus of claim 51, wherein the stent comprises a biodegradable material.

53. The apparatus of claim 50, wherein the implant comprises microparticles.

54. The apparatus of claim 53, wherein the microparticles comprise a biodegradable material.

55. The apparatus of claim 50, wherein the implant comprises microspheres.

56. The apparatus of claim 55, wherein the microspheres comprise a biodegradable material.

57. The apparatus of claim 50, wherein the implant comprises a drug releasing material.

58. The apparatus of claim 57, wherein the drug releasing material contains a drug effective in the treatment of glaucoma.

59. An apparatus for treating ocular disease in a patient, comprising:

a locating device, the locating device having a tissue contacting surface configured for contacting an exterior surface of the patient's eye, the locating device adapted for non-invasively locating Schlemm's Canal within the patient's eye;

a microsurgical device;

and a surgical access device physically coupled to the locating device for guiding the microsurgical device in relation to the locating device, the surgical access device having a cantilever beam that extends axially with respect to the tissue contacting surface of the locating device, a guiding sleeve coupled to the cantilever beam, an angle adjustment mechanism for adjusting an angle of the guiding sleeve with respect to the tissue contacting surface of the locating device and a mechanism for advancing the microsurgical device through the guiding sleeve and into Schlemm's Canal within the patient's eye wherein the microsurgical device comprises a microcannula slidably positioned within the guide sleeve; and wherein the mechanism for advancing the microsurgical device through the guiding sleeve and into Schlemm's Canal within the patient's eye comprises a thumbwheel configured to engage a lead screw connected to the microcannula.

60. The apparatus of claim 59, wherein the surgical access device is configured to deliver the microsurgical device into Schlemm's Canal along a path spaced apart distally from the tissue contacting surface of the locating device and approximately parallel to the tissue contacting surface of the locating device.

61. The apparatus of claim 59, further comprising a handle having a longitudinal axis, wherein the tissue contacting surface is approximately perpendicular to the longitudinal axis of the handle, and wherein the surgical access device is configured to deliver the microsurgical device into Schlemm's Canal along a path approximately perpendicular to the longitudinal axis of the handle.

62. The apparatus of claim 59, wherein the locating device comprises an ultrasound imaging transducer, and wherein the apparatus further comprises an image processing system and a display device for displaying an ultrasound image of the eye produced by the ultrasound imaging transducer of the locating device, the ultrasound image of the eye providing a visual indication of when Schlemm's Canal is located in the imaging plane of the locating device distal to the tissue contacting surface of the locating device.

63. An apparatus for treating ocular disease in a patient, comprising:

a locating device, the locating device having a tissue contacting surface configured for contacting an exterior surface of the patient's eye, the locating device adapted for non-invasively locating Schlemm's Canal within the patient's eye;

a microsurgical device;

and a surgical access device physically coupled to the locating device for guiding the microsurgical device in relation to the locating device, the surgical access device having a cantilever beam that extends axially with respect to the tissue contacting surface of the locating device, a guiding sleeve coupled to the cantilever beam, an angle adjustment mechanism for adjusting an angle of the guiding sleeve with respect to the tissue contacting surface of the locating device and a mechanism for advancing the microsurgical device through the guiding sleeve and into Schlemm's Canal within the patient's eye;

wherein the microsurgical device comprises a microcannula slidably positioned within the guide sleeve and an inflatable dilating balloon mounted on a distal end of the microcannula.

64. The apparatus of claim 63, wherein the mechanism for advancing the microsurgical device through the guiding sleeve and into Schlemm's Canal within the patient's eye comprises a thumbwheel configured to engage a lead screw connected to the microcannula.

* * * * *